United States Patent [19]

Okuyama et al.

[11] Patent Number: 5,352,704
[45] Date of Patent: Oct. 4, 1994

[54] GUANIDINOBENZENE DERIVATIVES

[75] Inventors: Akira Okuyama; Kyozo Naito; Hidetoshi Ogino; Toshio Nagase; Kiyofumi Ishikawa; Nobuo Tanaka, all of Meguro, Japan

[73] Assignee: Banyu Pharmaceutical Co., Ltd., Tokyo, Japan

[21] Appl. No.: 963,528

[22] Filed: Oct. 20, 1992

Related U.S. Application Data

[63] Continuation of Ser. No. 630,985, Dec. 24, 1990, abandoned.

[30] Foreign Application Priority Data

Dec. 22, 1989 [JP] Japan .................. 1-334188

[51] Int. Cl.$^5$ .................. A61K 31/165; C07C 233/64
[52] U.S. Cl. .................. 514/619; 564/168
[58] Field of Search ............... 564/168, 230, 237, 238, 564/164; 514/619, 620, 634, 631

[56] References Cited

U.S. PATENT DOCUMENTS

| 3,824,267 | 7/1974 | Ito et al. | 562/439 |
|---|---|---|---|
| 4,514,416 | 4/1985 | Fugii et al. | 549/442 |
| 4,820,730 | 4/1989 | Fugii et al. | 514/510 |
| 4,851,441 | 7/1989 | Higa et al. | 564/237 |

FOREIGN PATENT DOCUMENTS

| 0214429 | 3/1987 | European Pat. Off. | |
| 2456731 | 5/1979 | France . | |
| 2-207021 | 8/1990 | Japan | A61K 31/245 |
| 2-243624 | 9/1990 | Japan | A61K 31/24 |
| 2-262516 | 10/1990 | Japan | A61K 31/245 |

*Primary Examiner*—Shailendra Kumar
*Attorney, Agent, or Firm*—Wegner, Cantor, Mueller & Player

[57] ABSTRACT

A guanidinobenzene derivative represented by the formula (I):

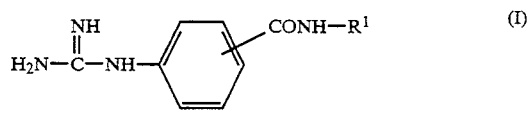

wherein $R^1$ represents a substituent selected from the group consisting of a phenyl group substituted by an amidino group and a naphthyl group substituted by an amidino group, and salt thereof; a process for the production thereof; and an antiviral pharmaceutical composition comprising the compound.

2 Claims, No Drawings

GUANIDINOBENZENE DERIVATIVES

This application is a continuation of U.S. application Ser. No. 07/630,985 filed Dec. 24, 1990, now abandoned.

BACKGROUND OF THE INVENTION

1. Field of the Invention

The present invention relates to novel guanidinobenzene derivatives, a process for the production thereof, and an antiviral agent comprising a guanidinobenzene derivative. These derivatives are useful for the treatment for various viral-related diseases.

2. Description of the Related Art

Japanese Unexamined Patent Application (KOKAI) No. 49-24917 discloses thiol esters of guanidino organic acid having an antiviral activity represented by the general formula:

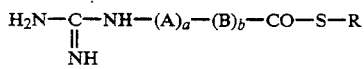

wherein A represents a linear or branched alkylene group having 1 to 10 carbon atoms; B represents p-phenylene group or a cycloalkylene group; a represents 0 or 1; b represents 0 or 1; a+b totals 1 or 2; R represents a linear or branched alkyl group having 1 to 10 carbon atoms, a carboethoxyalkyl group having 1 to 10 carbon atoms, a cycloalkyl group, an aromatic group or a phenylalkyl group, wherein the cycloalkyl group and the aromatic group can be substituted with a lower alkyl group, a carboethoxy group, a carboethoxy-lower alkyl group, a carboxyalkyl group, a halogen atom, an alkoxy group, an arylamide group, an alkylsulfonyl group, a carboxy group, a thiocarboxy group, a mercaptocarboxy group, a nitro group or a carbamoyl group. These types of compounds, however, exhibit an antiviral activity that is too weak for practical use.

In addition, as different types of antiviral agents, various kinds of nucleic acid derivatives are known; for example, amantadine, etc., are known as anti-influenza virus agents. The nucleic acid derivative type antiviral agents, however, cause side-effects such as liver function disorder, mutagenity and subacute toxicity, and the amantadine causes side effects such as teratogenicity, and further, the higher the frequency of use, the lower becomes efficacy (Virology, Raven Press, pp 323–348, 1985).

Therefore, new antiviral agents not having the above-mentioned drawback are urgently required.

SUMMARY OF THE INVENTION

Accordingly, the present invention provides new guanidinobenzene derivatives having a potent antiviral activity and less side effects, represented by the formula (I):

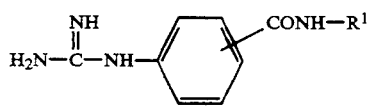

wherein R$^1$ represents a substituent selected from the group consisting of a phenyl group substituted by an amidino group and a naphthyl group substituted by an amidino group.

Moreover, the present invention provides a process for the production of the guanidinobenzene derivatives, comprising the step of reacting a guanidinobenzoic acid represented by the formula (II):

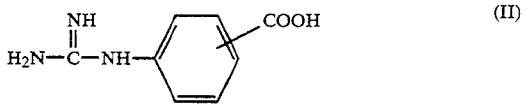

or an acid addition salt thereof with an amine compound represented by the formula (III):

wherein R$^1$ represents a substituent selected from the group consisting of a phenyl group substituted by an amidino group and a naphthyl group substituted by an amidino group, or an acid addition salt thereof, in an inert solvent.

Moreover, the present invention provides an antiviral pharmaceutical composition comprising one of the above-mentioned guanidinobenzene derivatives and a pharmaceutically acceptable carrier.

DESCRIPTION OF THE PREFERRED EMBODIMENTS

As the present guanidinobenzene derivatives, the following compounds are exemplified:

(1) 4-Guanidinobenzoic acid 4-amidinobenzamide,
(2) 4-Guanidinobenzoic acid 3-amidinobenzamide,
(3) 4-Guanidinobenzoic acid 2-amidinobenzamide,
(4) 3-Guanidinobenzoic acid 4-amidinobenzamide,
(5) 3-Guanidinobenzoic acid 3-amidinobenzamide,
(6) 3-Guanidinobenzoic acid 2-amidinobenzamide,
(7) 2-Guanidinobenzoic acid 4-amidinobenzamide,
(8) 2-Guanidinobenzoic acid 3-amidinobenzamide,
(9) 2-Guanidinobenzoic acid 2-amidinobenzamide,
(10) 4-Guanidinobenzoic acid 2-amidino-1-naphthylamide,
(11) 4-Guanidinobenzoic acid 3-amidino-1-naphthylamide,
(12) 4-Guanidinobenzoic acid 4-amidino-1-naphthylamide,
(13) 4-Guanidinobenzoic acid 5-amidino-1-naphthylamide,
(14) 4-Guanidinobenzoic acid 6-amidino-1-naphthylamide,
(15) 4-Guanidinobenzoic acid 7-amidino-1-naphthylamide,
(16) 4-Guanidinobenzoic acid 8-amidino-1-naphthylamide,
(17) 3-Guanidinobenzoic acid 2-amidino-1-naphthylamide,
(18) 3-Guanidinobenzoic acid 3-amidino-1-naphthylamide,
(19) 3-Guanidinobenzoic acid 4-amidino-1-naphthylamide,
(20) 3-Guanidinobenzoic acid 5-amidino-1-naphthylamide,
(21) 3-Guanidinobenzoic acid 6-amidino-1-naphthylamide,
(22) 3-Guanidinobenzoic acid 7-amidino-1-naphthylamide,

(23) 3-Guanidinobenzoic acid 8-amidino-1-naphthylamide,
(24) 2-Guanidinobenzoic acid 2-amidino-1-naphthylamide,
(25) 2-Guanidinobenzoic acid 3-amidino-1-naphthylamide,
(26) 2-Guanidinobenzoic acid 4-amidino-1-naphthylamide,
(27) 2-Guanidinobenzoic acid 5-amidino-1-naphthylamide,
(28) 2-Guanidinobenzoic acid 6-amidino-1-naphthylamide,
(29) 2-Guanidinobenzoic acid 7-amidino-1-naphthylamide,
(30) 2-Guanidinobenzoic acid 8-amidino-1-naphthylamide,
(31) 4-Guanidinobenzoic acid 1-amidino-2-naphthylamide,
(32) 4-Guanidinobenzoic acid 3-amidino-2-naphthylamide,
(33) 4-Guanidinobenzoic acid 4-amidino-2-naphthylamide,
(34) 4-Guanidinobenzoic acid 5-amidino-2-naphthylamide,
(35) 4-Guanidinobenzoic acid 6-amidino-2-naphthylamide,
(36) 4-Guanidinobenzoic acid 7-amidino-2-naphthylamide,
(37) 4-Guanidinobenzoic acid 8-amidino-2-naphthylamide,
(38) 3-Guanidinobenzoic acid 1-amidino-2-naphthylamide,
(39) 3-Guanidinobenzoic acid 3-amidino-2-naphthylamide,
(40) 3-Guanidinobenzoic acid 4-amidino-2-naphthylamide,
(41) 3-Guanidinobenzoic acid 5-amidino-2-naphthylamide,
(42) 3-Guanidinobenzoic acid 6-amidino-2-naphthylamide,
(43) 3-Guanidinobenzoic acid 7-amidino-2-naphthylamide,
(44) 3-Guanidinobenzoic acid 8-amidino-2-naphthylamide,
(45) 2-Guanidinobenzoic acid 1-amidino-2-naphthylamide,
(46) 2-Guanidinobenzoic acid 3-amidino-2-naphthylamide,
(47) 2-Guanidinobenzoic acid 4-amidino-2-naphthylamide,
(48) 2-Guanidinobenzoic acid 5-amidino-2-naphthylamide,
(49) 2-Guanidinobenzoic acid 6-amidino-2-naphthylamide,
(50) 2-Guanidinobenzoic acid 7-amidino-2-naphthylamide, and
(51) 2-Guanidinobenzoic acid 8-amidino-2-naphthylamide.

Acid addition salts of the present invention are preferably pharmaceutically acceptable acid addition salts and, for example, include salts of an inorganic acid such as hydrochloric acid, sulfuric acid, carbonic acid or phosphoric acid, or salts of an organic acid such as acetic acid, lactic acid, citric acid, methanesulfonic acid, p-toluenesulfonic acid, succinic acid, fumaric acid or maleic acid.

Compounds of the present invention represented by the formula (I) can be prepared, for example, by reacting a guanidinobenzoic acid represented by the formula (II):

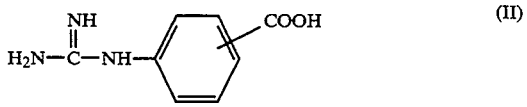

or an acid addition salt thereof with an amino compound represented by the formula (III):

wherein $R^1$ represents a substituent selected from the group consisting of a phenyl group substituted by an amidino group and a naphthyl group substituted by an amidino group, or an acid addition salt thereof.

The above-mentioned reaction is preferably carried out in an inert solvent, for example, an aprotic polar solvent such as pyridine, methylene chloride, N,N-dimethylformamide or dimethylsulfoxide, or a mixture thereof, at $-20°$ C. to a room temperature, preferably at $-10°$ C. to $0°$ C., in the presence of a condensation agent such as dicyclohexylcarbodiimide or 1-(3-dimethylaminopropyl)-3-ethylcarbodiimide, for 5 to 24 hours.

In this process the acid addition salts of the compounds (II) and (III) used as starting materials are, for example, those of hydrochloric acid, sulfuric acid or phosphoric acid, preferably the salt of hydrochloric acid.

To isolate and purify the present compound from a reaction mixture obtained as described above, for example, the solvent is evaporated from the reaction mixture, to give a residue, which is then suspended in an alcohol such as methanol, ethanol or isopropanol, and a saturated sodium bicarbonate aqueous solution is added thereto to afford a carbonate of the present compound.

The thus-obtained carbonate of the present compound can be converted to another salt by adding a mixture of water and an alcohol such as methanol or ethanol to the carbonate, followed by the addition of an appropriate acid. If a further purification is desired, the above-mentioned procedure can be repeated.

The compounds represented by the formula (II) and (III) and acid addition salts thereof, used as starting materials for the production of the present compounds are commercially available, or can be easily produced according to a procedure described in *J. Am. Chem. Soc.*, Vol. 65, 239–242, 1943, or *Pharmazie*, Vol. 34, 227–228, 1979.

The present compounds are useful for the treatment of viral infection diseases caused by, for example, an envelope virus such as a retrovirus, for example, influenza virus,, parainfluenza virus, herpesvirus, or human immunodeficiency virus (HIV).

An antiviral pharmaceutical composition of the present invention comprising a compound of the formula (I) can be administered through various routes, and the effective dose of the compound varies depending on the administration route used, as well as the age, sex, body weight and other conditions of a patient. For example, for an oral administration, the effective dose is 1 to 500 mg per administration, which is administered 1 to 3 times a day; for a rectal administration, 1 to 100 mg per administration, 1 to 3 times a day; for inhalation to the bronchia, 0.1 to 500 mg per one inhalation, 2 to 3 times a day; for an intravenus administration, 0.1 to 10 mg per administration, 1 to 2 times a day; for an intranasal administration, 0.1 to 500 mg per administration, 2 to 4 times a day; for eye dropping, 0.1 to 50 mg per administration, 3 to 4 times a day; and as an ointment, 1 to 500 mg per administration, 1 to 3 times a day.

The present pharmaceutical composition can be formulated in any way corresponding to the administration route thereof as described above, and this includes enteral and parenteral formulations.

For an oral administration, the present pharmaceutical composition is preferably formulated in a unit dose form, such as tablets, troches, powders, dragee, particles or capsules. For the formulation of these compositions, a binder such as gum arabic, gelatin, sorbitol, tragacanth gum, polyvinyl pyrolidon, polyvinyl alcohol, hydroxypropyl methyl cellulose, methyl cellulose, crystalline cellulose or sodium carboxymethyl cellulose; a filler such as lactose, sucrose, mannitol, potato starch, calcium phosphate, sorbitol or crystalline cellulose; a lubricant such as magnesium stearate, talc, polyethylene glycol or silica; and/or a disintegration agent such as potato starch, lower-substituted hydroxypropyl cellulose, calcium carboxymethyl cellulose or sodium carboxymethyl starch, alone or in combination, are used. Soft capsule may contain a conventional vehicle such as plant oil, polyethylene glycol or glycerol, or an oily suspending agent given hereinafter, a solution, or a wetting agent such as surfactant.

A liquid formulation is, for example, an aqueous or oily suspension, solution, syrup or elixir. Alternatively, a lyophyilized product may be reconstructed to form a liquid formulation immediately prior to use. For the liquid formulation, a suspension agent such as methyl cellulose, sodium carboxymethyl cellulose, hydroxypropyl cellulose, hydroxypropyl methyl cellulose, polyvinyl pyrolidon, polyvinyl alcohol, tragacanth gum, gelatin or sodium alginate; an emulsifier such as lecithin, sorbitan, fatty acid ester, gum arabic or tragacanth gum; a wetting agent such as polyoxyethylene sorbitan fatty acid ester, polyoxyethylene fatty acid ester, hydrogenated ricinus oil, sesame oil, soybean oil, propylene glycol, polyethylene glycol or ethyl alcohol; a preservative such as methyl p-hydroxybenzoate, propyl p-hydroxybenzoate or sorbic acid, and an additive such as simple syrup, sucrose, sorbitol or mannitol, may be used alone or in combination.

As a base for a rectal administration formulation, an oily base such as cocoa butter, wite psol or triglyceride, or a water soluble base such as glycerol, glycerogelatin or macrogol is used.

An additive for an injection formulation includes a dissolving aid such as polyoxyethylene, hardened ricinus oil or sodium benzoate, an osmotic pressure-adjusting agent such as glucose, sodium chloride or glycerol; a stabilizer such as sodium sulfite, anhydrous sodium sulfite, sodium metabisulfite or glycerol may be used alone or in combination.

For an inhalation to a respiratory organ such as the bronchia or nose, an aerosol, inhalation solution, liquid, powders, capsules or ointment can be used. The aerosol may be an oily aerosol comprising a non-ionic surfactant such as alacel or Span 80, an ampholytic surface active agent such as lecitin, or a dispersant such as oleylalcohol, and a propellant such as butane or Freon (TM); or an aqueous aerosol comprising an osmotic pressure-adjusting agent such as physiological saline, phosphate buffer or acetate buffer, and purified water or injectable distilled water. For the liquid formulation, for example, polyethylene glycol, sorbitol, polysorbate or physiological saline may be used as a carrier. For powders, for example, crystalline cellulose, α-cellulose, cross-linked sodium carboxymethyl cellulose, hydroxypropyl cellulose, carboxymethyl starch or amylose may be used as a carrier. In addition, these powders may be filled in a capsule. For an ointment, for example, polyethylene glycol, hydroxyethyl cellulose, methyl cellulose, carboxymethyl cellulose, hydroxypropyl cellulose or the like may be used as a carrier. Moreover, the active ingredient may be placed on the mucosa by inhalation or a nasal application, to deliver the ingredient in a sustained manner. For this purpose, the formulation may contain, for example, a cellulose ether such as methyl cellulose, ethyl cellulose, propyl cellulose, hydroxyethyl cellulose, carboxyethyl cellulose or hydroxypropyl cellulose, or a synthetic polymer such as polyacrylate or carboxyvinyl polymer, as the base material.

These pharmaceutical compositions can be prepared according to a conventional procedure.

The present pharmaceutical composition may contain one of the present compounds in an amount of about 0.1 to 100%, preferably 0.5 to 90%, by weight of the composition.

Next, the antiviral activity of the present compound is demonstrated by the following pharmacological tests.

In the tests the following compounds:
Compound A: 4-guanidinobenzoic acid 4-amidinobenzamide.2 methanesulfonate; and
Compound B: 4-guanidinobenzoic acid 6-amidino-2-naphthylamide.2 methanesulfonate, were used.

Pharmacological test 1. Inhibitory action on plaque formation by human influenza virus The inhibitory activity of the present compounds A and B on plaque formation by human influenza virus A/WSN was measured according to a method described in Virology Vol. 29, 84–91, 1966.

Namely, $1 \times 10^6$ MDCK cells (dog kidney cells) were inoculated in 6 cm plastic dish containing D-MEM medium, and cultured in a $CO_2$ incubator for 24 hours, and after discarding the medium, 0.1 ml of a diluted virus solution containing about 50 plaque forming units of human influenza virus A/WSN was added to the cultured cells. After shaking, the dish was allowed to stand at room temperature for 30 minutes, a solubilized agar containing a desired amount of a test compound was overlayed. After 3 days culture, the agar layer was removed, and cells were stained with a staining solution to count the number of plaques. Next, a plaque formation inhibition ratio was calculated according to the following equation. The result is shown in Table 1.

Inhibition ratio $(\%) = (1 - T/C) \times 100$
wherein

T: mean number of plaques in the presence of a test compound;

C: mean number of plaques of control.

Note, in the above test, the D-MEM medium, the solution for diluting the virus, the upper layer agar, and the staining solution were prepared as follows:

[D-MEM medium]

First, 9.5 g of powder of Dulbecco's Modified EAGLE MEDIUM "Nissui" was dissolved in 1 l of distilled water (the resulting solution is designated 1*DMEM hereinafter), and the solution was autoclaved. L-glutamine (0.584 g), filtered aqueous solution of kanamycin (0.1 g), and 20 ml of a 7.5% sodium bicarbonate, and 110 ml of heat-inactivated fetal bovine serum were added thereon.

[Solution for dilution of virus]

First, 10 g of calcium chloride, 10 g of magnesium chloride, and 5.8 ml of 30% bovine serum albumin were dissolved in 1 l of a phosphate buffered saline, and the solution was filtered before use.

[Upper layer agar]

| | |
|---|---|
| A: Distilled water | 16 ml |
| 2*DMEM + bovine serum albumin | 50 ml |
| 1% DEAE dextran | 1 ml |
| 7.5% sodium bicarbonate aqueous solution | 2 ml |
| B: 2.0% agar (Noble) | 30 ml |
| Filtrated A solution was added to autoclaved solubilized agor. | |
| [2*DMEM + bovine serum albumin] | |
| 4*Dulbecco | 250 ml |
| 1M HEPES | 10 ml |
| 10% bovine serum albumin | 20 ml |
| 7.5% sodium bicarbonate aqueous solution | 16 ml |
| 6%-glutamine aqueous solution | 10 ml |
| 10% kanamycin aqueous solution | 1 ml |
| Distilled water | 193 ml |

The solutions were mixed and filtered before use.

[Staining solution]

Alter dissolving 100 mg of crystal violet in 20 ml of ethanol, 80 ml of water was added thereto.

TABLE 1

| Text sample | Concentration ($\mu$g/ml) | Inhibition ratio(%) of plaque formation |
|---|---|---|
| Compound A | 12.5 | 2.9 |
| | 25 | 51.0 |
| | 50 | 80.8 |
| Compound B | 10 | 31.4 |
| | 20 | 67.6 |
| | 50 | 82.4 |

Pharmacological test 2

The growth inhibitory activity of compound B on influenza virus in the lung of hamsters was tested according to J. Mills, *The Journal of Infectious Diseases*, Vol. 123, 145-157, 1971.

Namely, anesthetized mole hamster was intranasally infected with 0.1 ml of a virus solution containing $3.8 \times 10^3$ PFU of influenza virus A/Udron/72 (H3N2) grown in a growing chicken egg. At 6, 11 and 24 hours after the infection, 50 $\mu$l of test solution containing the compound B in 3.3% hydroxypropyl cellulose solution was intranasally administered. After 28 hours from the infection the hamster was sacrificed by the anesthesia, and the lung was removed. The lung was thoroughly homogenized in a mortar with sea sand, and the homogenate was centrifuged. An amount of virus contained in the resulting supernatant was measured as plaque forming ability in dog kidney cells. The results are shown in Table 2.

TABLE 2

| Test compound | Concentration (mg/ml) | Number of animals | PFU/lung | % Inhibition |
|---|---|---|---|---|
| Control | — | 5 | $4.8 \pm 2.2 \times 10^5$ | — |

TABLE 2-continued

| Test compound | Concentration (mg/ml) | Number of animals | PFU/lung | % Inhibition |
|---|---|---|---|---|
| Compound B | 10.0 | 5 | $5.0 \pm 10.0 \times 10^3$ | 99.0** |

**P < 0.01, t-Test

As shown in Table 2, compound of the present invention strongly inhibited the growth of influenza virus in lungs of the hamster.

Therefore, since the present compounds efficiently inhibit the growth of envelope viruses such as human influenza virus, they are useful for the treatment of diseases due to viral infections.

EXAMPLES

The present invention will now be further illustrated by, but is by no means limited to, the following examples.

Example 1.

4-Guanidinobenzoic acid 4-amidinobenzamide.2 methanesulfonate

First, 100 mg of 4-guanidinobenzoic acid.hydrochloride and 145 mg of 4-amidinobenzamidine.2 hydrochloride were suspended in 2 ml of absolute pyridin, and after adding 133 mg of 1-(3-dimethylaminopropyl)-3-ethylcarbodiimide.hydrochloride thereto, the mixture was stirred at room temperature for 19 hours. The solvent was distilled off under reduced pressure at 30° C., and after drying under reduced pressure, the resulting residue was suspended in ethanol. Then, a saturated sodium bicarbonate aqueous solution was added to the suspension, and the resulting precipitate was filtered. The precipitate was washed with water and acetone, and suspended in methanol, and methanesulfonic acid was added thereto to dissolve the precipitate. Then, the solution was triturated with ethyl ether to afford the methanesulfonate, which was then filtered and dried in vacuo to give 59.2 mg of the title compound as an off-white powder.

Melting point: 264° C.-265° C. (2 methanesulfonate)
High resolution FAB-MS (for $(C_{15}H_{16}N_6O+H)^+$)
Calculated: 297.1464
Found: 297.1443
IR (cm$^{-1}$, KBr): 3340, 3172, 1683, 1608, 1575, 1509, 1338, 1197, 1044
$^1$H-NMR ($\delta$, DMSO-d$_6$): 2.35 (s, 6H), 7.40 (d, J=8.9 Hz, 2H), 7.67 (s, 4H), 7.85 (d, J=8.9 Hz, 2H), 8.03 (d, J=8.9 Hz, 2H), 8.07 (d, J=8.9 Hz, 2H), 8.88 (s, 2H), 9.22 (s, 2H), 9.99 (s, 1H), 10.65 (s, 1H).

Example 2.

4-Guanidinobenzoic acid 6-amidino-2-naphthylamide.2 methanesulfonate

First, 100 mg of 6-amino-2-naphthoamidine.2 hydrochloride and 86.6 mg of 4-guanidinobenzoic acid hydrochloride were condensed to afford an amide hydrochloride according to the same procedure described in Example 1, and the amide hydrochloride was converted to the corresponding carbonate according to the same procedure described in Example 1, for purification. Then methanesulfonic acid was added to a suspension of the carbonate to obtain 17.10 mg of the title compound as a pale yellow amorphous solid.

High resolution FAB-MS (for $(C_{19}H_{18}N_6O+H)^+$)

Calculated: 347.1620
Found: 347.1621

$^1$H-NMR (δ, DMSO-d$_6$): 2.32 (s, 6H), 7.40 (d, J=8.9 Hz, 2H), 7.62 (brs, 4H), 7.79 (dd, J=8.9, 1.9 Hz, 1H), 7.98 (dd, J=8.9, 1.7 Hz, 1H), 8.09 (dd, J=8.9, 1.6 Hz, 4H), 8.42 (d, J=1.9 Hz, 1H), 8.63 (d, J=1.7 Hz, 1H), 8.97 (brs, 2H), 9.37 (brs, 2H), 9.93 (brs, 1H), 10.63 (brs, 1H).

Example 3

First, 10 g of 4-guanidinobenzoic acid 4-amidinobenzimide.2 methanesulfonate, 300 g of polyethylene glycol 400 and 0.5 g of polysolivate 80 were stirred while heated, to form a homogeneous solution and a nasal liquid formulation, which could be intranasally administered in a unit dose of 0.1 ml.

Example 4

First, 200 mg of 4-guanidinobenzoic acid 6-amidino-2-naphthylamide.2 methanesulfonate and 100 mg of hydroxypropyl cellulose were thoroughly triturated in a mortar to form a homogeneous powder, which was filled in capsules to prepare intranasal capsules.

Example 5

First, 50 mg of 4-guanidinobenzoic acid 4-amidinobenzamide.2 methanesulfonate and 50 mg of hydroxypropyl cellulose were dissolved in 5 ml of injectible distilled water, and the solution then lyophilized to form a homogeneous solid composition, which was then filled in capsules to obtain intranasal capsules.

Example 6

First, 1.0 g of 4-guanidinobenzoic acid 6-amidino-2-naphthylamide.2 methanesulfonate 2.5 g of hydroxypropyl cellulose and 20 g of carbopale were homogeneously mixed, and 0.5 g of magnesium stearate was added to the mixture. The mixture was compressed to form 10 plane tablets, and one tablet was applied to the mucosa in mouth.

We claim:

1. A guanidinobenzene derivative represented by the formula (I):

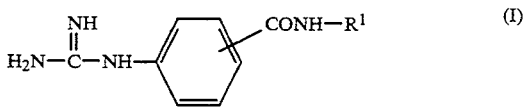

wherein R$^1$ represents a substituent selected from the group consisting of a phenyl group substituted by an amidino group and a naphthyl group substituted by an amidino group or a pharmaceutically acceptable acid addition salt thereof.

2. An antiviral pharmaceutical composition comprising a compound represented by the formula (I) according to claim 1, and a pharmaceutically acceptable carrier.

* * * * *